US008692717B2

(12) United States Patent
Friedman

(10) Patent No.: US 8,692,717 B2
(45) Date of Patent: Apr. 8, 2014

(54) ANTENNA FOR THORACIC RADIO INTERROGATION

(75) Inventor: Robert Friedman, Las Vegas, NV (US)

(73) Assignee: Noninvasive Medical Technologies, Inc., Las Vegas, NV (US)

( * ) Notice: Subject to any disclaimer, the term of this patent is extended or adjusted under 35 U.S.C. 154(b) by 996 days.

(21) Appl. No.: 12/383,356

(22) Filed: Mar. 23, 2009

(65) Prior Publication Data

US 2009/0240132 A1    Sep. 24, 2009

Related U.S. Application Data

(63) Continuation-in-part of application No. PCT/US2007/020492, filed on Sep. 21, 2007.

(60) Provisional application No. 60/846,408, filed on Sep. 21, 2006, provisional application No. 60/910,394, filed on Apr. 5, 2007, provisional application No. 60/973,970, filed on Sep. 20, 2007.

(51) Int. Cl.
    *A61B 5/00*    (2006.01)

(52) U.S. Cl.
    USPC ........................... 343/700 MS; 600/407

(58) Field of Classification Search
    USPC ................. 600/407, 430, 481, 529, 547; 343/700 MS, 829, 702, 718
    See application file for complete search history.

(56) References Cited

U.S. PATENT DOCUMENTS

| 3,483,860 | A |   | 12/1969 | Namerow |           |
|-----------|---|---|---------|---------|-----------|
| 4,083,046 | A | * | 4/1978  | Kaloi   | 343/700 MS |
| 4,151,532 | A |   | 4/1979  | Kaloi   |           |
| 4,700,194 | A | * | 10/1987 | Ogawa et al. | 343/700 MS |
| 4,926,868 | A |   | 5/1990  | Larsen  |           |
| 4,981,141 | A |   | 1/1991  | Segalowitz |        |
| 5,068,886 | A |   | 11/1991 | Lavia   |           |
| 5,309,917 | A |   | 5/1994  | Wang et al. |       |
| 5,404,877 | A |   | 4/1995  | Nolan et al. |      |
| 5,423,326 | A |   | 6/1995  | Wang et al. |       |
| 5,443,073 | A |   | 8/1995  | Wang et al. |       |
| 5,791,349 | A |   | 8/1998  | Shmulewitz |        |

(Continued)

FOREIGN PATENT DOCUMENTS

| CN | 2629236 Y   | 7/2004  |
|----|-------------|---------|
| EP | 0395015 A2  | 10/1990 |

(Continued)

OTHER PUBLICATIONS

Liu et al. T-coupled Circular Microstrip Antenna with H-shaped Aperture for Bandwidth and Radiation-Gain Improvements. Microwave and Optical Technology Letters vol. 37 No. 6, Jun. 20, 2003, pp. 414-417.*

(Continued)

*Primary Examiner* — Unsu Jung
*Assistant Examiner* — Phong K Huynh
(74) *Attorney, Agent, or Firm* — Panitch Schwarze Belisario & Nadel LLP

(57) ABSTRACT

An antenna includes an antenna layer, a ground layer and a dielectric layer between the antenna layer and the ground layer. The antenna layer and the ground layer form a figure in the shape of two identical mirror image triangles joined together at a longest side of each one of the triangles where each side of each triangle is a different length.

22 Claims, 3 Drawing Sheets

(56) References Cited

U.S. PATENT DOCUMENTS

| | | |
|---|---|---|
| 5,945,950 A | 8/1999 | Elbadawy |
| 6,037,911 A * | 3/2000 | Brankovic et al. ..... 343/700 MS |
| 6,317,094 B1 | 11/2001 | Wu et al. |
| 6,342,855 B1 * | 1/2002 | Rothe .................... 343/700 MS |
| 6,370,433 B1 | 4/2002 | Hartlaub et al. |
| 6,409,675 B1 | 6/2002 | Turcott |
| 6,411,826 B1 | 6/2002 | Camp, Jr. |
| 6,600,949 B1 | 7/2003 | Turcott |
| 6,752,277 B1 | 6/2004 | Sempliner |
| 6,888,503 B2 * | 5/2005 | Shikata .................. 343/700 MS |
| 7,082,294 B2 | 7/2006 | Denis et al. |
| 7,099,631 B2 | 8/2006 | Lee et al. |
| 7,272,431 B2 | 9/2007 | McGrath |
| 7,474,918 B2 | 1/2009 | Frantz et al. |
| 2002/0054412 A1 | 5/2002 | Keller et al. |
| 2004/0249258 A1 | 12/2004 | Tupin et al. |
| 2006/0016800 A1 | 1/2006 | Paradiso et al. |
| 2006/0109180 A1 | 5/2006 | Fukuda |
| 2006/0145872 A1 | 7/2006 | Tanaka et al. |
| 2008/0269589 A1 | 10/2008 | Thijs et al. |
| 2009/0203972 A1 | 8/2009 | Heneghan et al. |
| 2009/0240133 A1 | 9/2009 | Friedman et al. |
| 2009/0240134 A1 | 9/2009 | Pal et al. |

FOREIGN PATENT DOCUMENTS

| | | |
|---|---|---|
| GB | 2349759 A | 11/2000 |
| WO | 2007033270 A2 | 3/2007 |
| WO | 2007096573 A1 | 8/2007 |
| WO | WO-2008036396 | 3/2008 |
| WO | WO-2008036402 | 3/2008 |
| WO | WO-2008036404 | 3/2008 |
| WO | WO-2008105837 | 9/2008 |

OTHER PUBLICATIONS

Office Action Issued Jun. 30, 2010 in CN Application No. 200780043164.0.

Int'l Prelminary Report on Patentability issued on Apr. 2, 2009 in Int'l Application No. PCT/US07/20473.

EP Search Report issued Jun. 20, 2011 in EP Application No. 07838633.1.

Pedersen et al, "Microwave Reflection and Transmission Measurements for Pulmonary Diagnosis and Monitoring", IEEE Transactions on Biomedical Engineering, vol. BME-25, No. 1, pp. 40-48 (1978).

Int'l Preliminary Report on Patentability issued Apr. 2, 2009 in Int'l Application No. PCT/US07/20487.

Int'l Preliminary Report on Patentability issued Apr. 2, 2009 in Int'l Application No. PCT/US07/20492.

* cited by examiner

ANTENNA FOR THORACIC RADIO INTERROGATION

CROSS-REFERENCE TO RELATED APPLICATIONS

This application is a continuation-in-part of PCT/US2007/020492 filed Sep. 21, 2007, entitled "Antenna for Thoracic Radio Interrogation" and claims the benefit of priority of U.S. Provisional application No. 60/846,408 entitled "Transducer-antenna-probe for Thoracic Radio Interrogation", filed Sep. 21, 2006; U.S. Provisional Application No. 60/910,394, entitled "Antenna for Thoracic Radio Interrogation", filed Apr. 5, 2007; and U.S. Provisional Application No. 60/973,970, entitled "Antenna for Thoracic Radio Interrogation", filed Sep. 20, 2007. All are incorporated by reference herein in their entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms to the extent and under the provisions as provided for by the terms of Contract No. DAH001-05-S-0144 awarded by the U.S. Air Force Special Operations Command (AFSOC).

BACKGROUND OF THE INVENTION

Hemodynamic monitoring, performed invasively with a pulmonary artery catheter, has become common in the care of the critically ill. Until recently, hemodynamic monitoring has been limited to the critical care unit, operating room and occasionally the emergency department, due to the invasive nature of the pulmonary artery catheter, the expertise required for insertion and maintenance of the catheter, and the close vigilance required to prevent potential vital risks to the patient. Accepted invasive hemodynamic monitoring methods include the Fick method, dye indicator dilution, and thermodilution.

Contact impedance cardiography systems now available provide a type of noninvasive monitoring of patient hemodynamics. Unlike invasive hemodynamic monitoring with a pulmonary artery catheter, noninvasive contact impedance monitoring is not restricted to care of the critically ill. Noninvasive continuous hemodynamic monitoring has utility in any clinical area, from the outpatient clinic to the critical care unit, where healthcare providers desire information regarding a patient's hemodynamic status without invasive procedure.

Conventional contact impedance cardiography operates by introducing an alternating current (AC) voltage test signal of low magnitude directly into the thorax. This is done using electrodes contacting the skin. The conductivity changes of the cardiac system, primarily blood flow through the heart, modulate the current introduced into the body by the voltage signal. The modulated current signal carries information that is compared to the original voltage test signal by a receiver/comparator to extract a cardiac impedance waveform. The direct current (DC) component of the modulated signal represents the fixed or baseline electrical impedance of the thorax, $Z_O$ and the AC component of the modulated signal represents the time varying cardiac impedance waveform $\Delta Z/\Delta t$ of the thorax. The conventional technology of contact impedance cardiography is disclosed and explained in U.S. Pat. Nos. 5,423,326, 5,443,073 and 5,309,917, incorporated by reference herein.

While contact impedance cardiography technology is a marked improvement over invasive technology, it still has some limitations. It requires the careful placement of several electrodes on the patient's torso. While this does not seem like a significant drawback, it has been an impediment to the movement of noninvasive continuous hemodynamic monitoring from the hospital emergency room to the medical first aid arena. Such medical first aid area encompasses virtually any emergency field situation including the military battle field, natural disaster, or other emergency medical scenario.

It has been discovered that the varying portions of a reflected radio interrogation signal can be processed in much the same way as the variations in the signals detected in conventional, contact impedance voltage measurements, to extract cardiac information. It will be appreciated that a reflected radio interrogation signal undergoes changes as a result of the encounters of the radio signal with different substances present in the human body. It has been found, in particular, that the reflected radio signal, like the much lower frequency impedance test signal conducted through the torso in conventional contact impedance measurement, is sensitive to electrically conductive substances and is modified in amplitude and phase at least in part by the dynamic changes of varying blood volume, flow velocity and possibly even alignment of the red blood cells that reflect the mechanical activity of the heart. The reflected radio interrogation signal, like the transmitted voltage test signal used in conventional, contact impedance measurement, has both a constant/baseline component (comparable to $Z_o$) and a component that varies relatively slowly over time (100 Hertz or less) comparable to $\Delta Z/\Delta t$, with at least first and second order components. Accordingly, like the transmitted test signal used in conventional, contact impedance measurement, the reflected radio interrogation signal carries information that can provide determination and even measurements of at least some of the same cardiac functions.

BRIEF SUMMARY OF THE INVENTION

Briefly stated the invention comprises an antenna including an antenna layer, a ground layer and a dielectric layer between the antenna layer and the ground layer. The antenna layer and the ground layer form a figure in the shape of two identical mirror image triangles joined together at a longest side of each one of the triangles where each side of each triangle is a different length.

In another aspect, the invention is a method of radiating an interrogation signal into a patient comprising the steps of configuring an antenna to have a return loss better than −10 dB when the antenna is proximate to the patient; placing the antenna proximate to the patient; and exciting the antenna with the interrogation signal.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
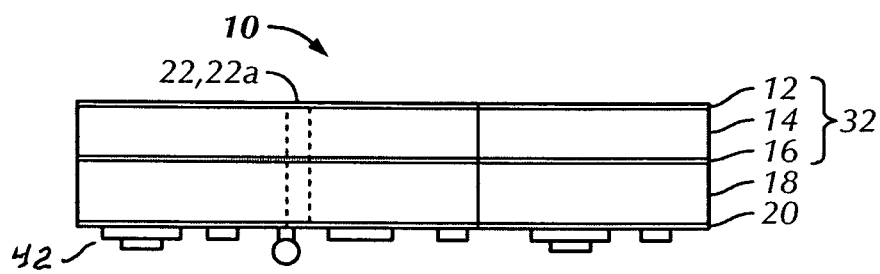
FIG. 1 is a side view of the preferred embodiment of an RFII antenna assembly.
Figure 2:
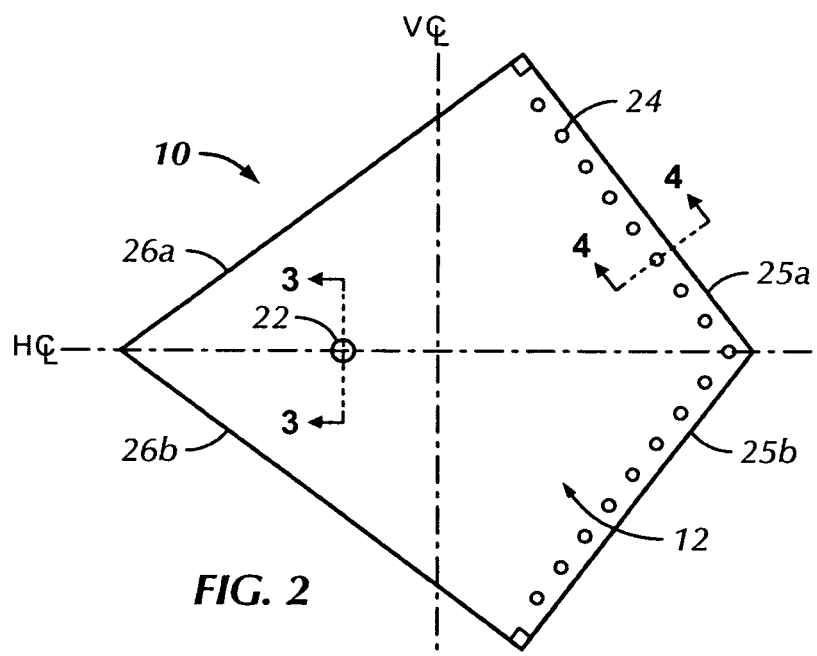
FIG. 2 is a plan view of a "bottom" side of the preferred embodiment of the RFII antenna assembly showing an antenna layer.
Figure 3:
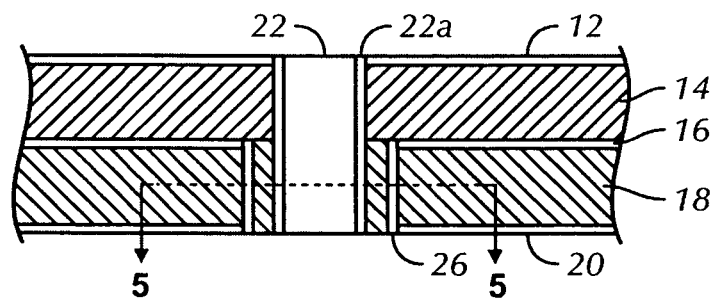
FIG. 3 is a cross sectional view of the preferred embodiment of the RFII antenna assembly taken through section A-A

Referring to FIGS. 1-3, there is shown in FIG. 1 a functional block diagram of a preferred embodiment of an RFII antenna assembly 10 for generating a radio frequency interrogation signal and for receiving and processing a reflected radio frequency interrogation signal. The RFII antenna assembly 10 comprises an antenna 32 and a measurement system components of which are indicated generally at 42. The measurement system 42 preferably includes a transmitter, a receiver and an on-board microprocessor to analyze the reflected radio frequency interrogation signal. When the RFII antenna assembly 10 is positioned proximate to a person to be monitored (hereafter patient), the microprocessor determines if the reflected radio frequency interrogation signal has Doppler modulation with good correlation to a valid cardiac impedance signal. The microprocessor may also determine additional characteristics of the reflected radio frequency interrogation signal such as hemodynamic parameters represented by the reflected radio frequency interrogation signal. The measurement system 42 may also include a second transmitter and a second antenna for wirelessly transmitting the microprocessor analysis of the reflected radio frequency interrogation signal to a remote location. Details of an exemplary measurement system 42 can be found in Application No. 60/973,985 previously incorporated by reference herein.

The RFII antenna assembly 10 preferably generates the radio frequency interrogation signal at a frequency within the 902-928 MHz industrial, scientific and medical (ISM) band and more preferably, generates the radio frequency interrogation signal at 915 MHz. However, as one skilled in the art would appreciate, the operating frequency of RFII antenna assembly 10 is not limited to the 902-928 MHz ISM band.

Referring to FIG. 1 there is shown a side view of the RFII antenna assembly 10. The RFII assembly 10 preferably comprises a laminate of five layers. Preferably, the antenna 32 comprises a copper antenna layer 12 on a bottom side of the RFII antenna assembly 10, a copper ground plane layer 16 and a dielectric layer 14 separating the antenna layer 12 from the ground plane layer 16. The antenna layer 12 is preferably formed of 0.5 oz copper and the ground layer 16 is preferably formed of 1.0 oz copper. However, the thickness of the copper is not critical. Preferably the material comprising the dielectric layer 14 has a dielectric constant of greater than 10 and dissipation factor of less than 0.003 at a frequency of 915 MHz. In the preferred embodiment of the antenna 32, the dielectric layer is provided by 25 mil thick Rogers 3210 ceramic filled laminate reinforced with woven fiberglass having a dielectric constant of 10.2. However, dielectric materials other than ceramic filled laminate could be used.

The measurement system 42 is preferably constructed on a printed circuit board (PCB) on a top side of the RFII antenna assembly 10. The PCB on which the measurement system 22 is constructed comprises a dielectric layer 18 and a printed circuit layer 20. In the preferred embodiment, the PCB layer 18 is made of 31 mil thick FR4 fiberglass epoxy-resin PCB material. However, other materials such as polyimide, ceramic or Teflon material could be used for the PCB material. The printed circuit layer 20 comprises circuit and ground patterns of 0.5 oz copper laminated to the PCB layer 18. A shown in FIGS. 1 and 3, a plated through hole 22, 22a provides a connection between the antenna layer 12 and the printed circuit layer 20 for providing the output of the transmitter to the antenna layer 12 and providing the output of the antenna layer 12 to the receiver.

In use, the RFII antenna assembly 10 is positioned by a user on the body of a human subject proximate to the heart region of the subject. The presently preferred RFII antenna assembly 10 is palm sized, and uses the single antenna 32 to both transmit and receive the radio signals. The radio transmitter of the measurement system 42 operably connected to the antenna 32 is configured to transmit an unmodulated radio interrogation signal of a predetermined fixed frequency through the antenna 32. The radio receiver operably connected to the antenna 32 is configured to capture through the antenna 32, reflections of the transmitted radio interrogation signal returned from the subject. The antenna assembly 10 is placed proximal the thorax, more particularly on a human subject's chest proximal the subject's heart and suggestedly opposite the center of the sternum, where it is aligned juxtaposed with the aorta. The antenna assembly 10 with measurement system 42 can be placed on the patient's clothing 35 as no direct skin contact is required by the present method and apparatus and clothing of natural or polymer materials does not affect passage of the radio waves. The antenna assembly 10 need only be sufficiently close to the thorax and aorta of the subject to receive usable reflections of the radio interrogation signal transmitted from the antenna assembly at a safe power level, for example, about one milliwatt. It has been found that usable reflected signals can be received with the antenna assembly 10 spaced up to about 10 mm from the subject's chest even when the radio interrogation signal is transmitted from antenna layer 12 at a strength of about one-half milliwatt. When the reflected radio frequency interrogation signal is found to be carrying the desired cardiac information, the microprocessor preferably generates a signal to the user that the antenna 32 is correctly positioned and that the desired cardiac data is being acquired.

Typically, an antenna for transmitting and/or receiving electromagnetic energy is designed and used to radiate/receive electromagnetic energy into/from air or free space. In contrast to a typical antenna, the antenna 32 is designed to transmit the electromagnetic energy of the radio frequency interrogation signal a very short distance, i.e. 0.01 cm to 10 cm, into the thoracic region of the human body. As would be understood by those skilled in the art, the resonant frequency, the driving point impedance and the return loss of a resonant antenna such as the antenna 32 is influenced by the permittivity, permeability and conductivity of the medium within the near field antenna 32. Because the permittivity, permeability and the conductivity of the human body differ significantly from that of free space, the dimensions of the antenna 32 and the location of the excitation point of the antenna 32 are different for operation when the patient is in the near field of the antenna 32.

A distance of 0.01 cm to 10 cm plus the few centimeters to the heart itself inside the chest is considered to be within the near field of the antenna 32 when the antenna 32 is excited by a signal at a frequency of 915 MHz. For the purposes of this application, the term proximate is used to identify when the antenna 32 is positioned such that a patient is within the near field of the antenna 32.

In the preferred embodiment of the RFII antenna assembly 10, the antenna 32 is a planar type of antenna commonly referred to as a patch antenna and preferably of one-quarter wavelength design. The preferred antenna 32 is approximately 2 inches long by less than 2 wide as will be explained below, the parameters of which are optimized to radiate an ultra-high frequency radio signal received from the transmitter a relatively short distance through a patient's clothing and into the thorax of the patient and at least into the heart, and to receive a returned radio signal generated by reflection from blood and other thoracic contents and provide that signal to the receiver.

Figure 6:
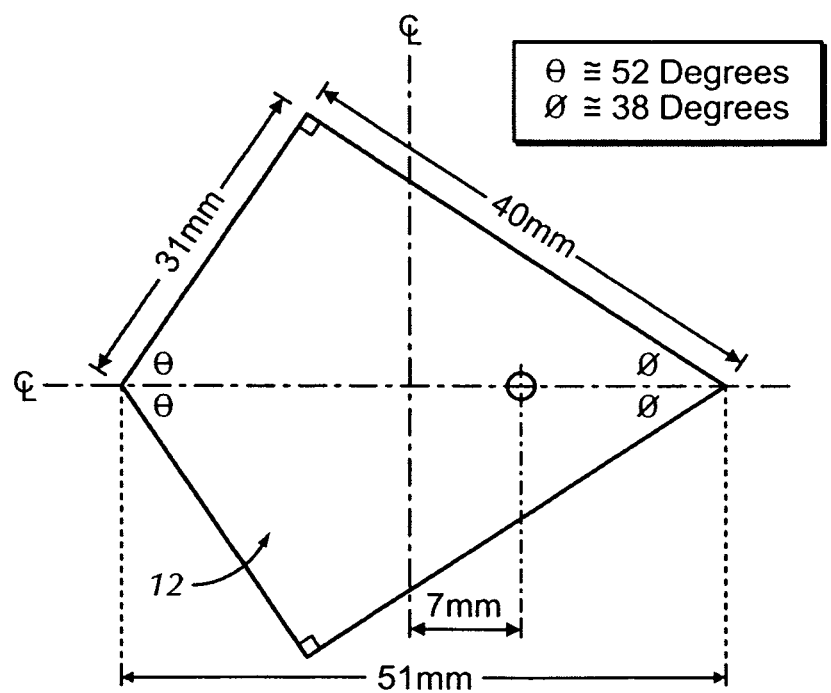
FIG. 6 is a diagram of the preferred embodiment of the antenna layer showing preferred dimensions of the antenna layer.

As shown in FIG. 2, the preferred embodiment of the antenna layer 12 and the ground layer 16 are each in the shape of two identical, nominally right triangles, the mirror images of each being joined together at the hypotenuse of each triangle to form a kite shaped antenna 32. For operation of the antenna 32 at 915 MHz, as shown in FIG. 6, the hypotenuse of each triangle, i.e. the length of the antenna 32, is preferably 51 mm, the length of the shorter side of each triangle is preferably 31 mm, and the length of the longer side of each triangle is preferably 40 mm. Consequently, the interior angles of each right triangle forming the preferred antenna 32 are nominally, 90, 52 and 38 degrees, making the angles of the four sided figure formed by the two triangles be 90, 104, 90, and 76 degrees respectively. The distance between the right angles can thus be calculated to be about 48 mm. Due to the kite shape, however, the actual area of layer 12 is still less than two square inches (12.4 sq. cm).

As one skilled in the art would understand, each dimension of the antenna 32 would be altered in inverse proportion to the frequency of the radio frequency interrogation signal should the radio frequency interrogation signal be changed from the preferred frequency of 915 MHz. Further, the acute interior angles of each right triangle are not limited to precisely 52 and 38 degrees. The angle of the smaller acute interior angle of each right triangle can be any angle between 31 and 44 degrees, and more preferably 35-40 degrees, with the larger acute angle being complementary, and the antenna 32 would still be within the spirit and scope of the invention.

Also, the antenna 32, when constructed of two triangles need not include an interior angle which is a right angle. Further, the antenna 32 need not be constructed of two identical mirror image right triangles but could be identical mirror image polygons joined together at the longest side of each polygon and having at least three of the sides of each polygon with different shapes.

The effect of the kite shape is to broaden the bandwidth of the antenna 32. Preferably, the bandwidth of the antenna 32 is such as to accommodate manufacturing tolerances in making the antenna 32 and any frequency uncertainty of the radio frequency interrogation signal. In the preferred embodiment, the 10 dB bandwidth of the antenna 32 is in the range of 14-30 MHz depending on the adjacent medium, but could be made larger or smaller by varying the shape of the antenna 32.

Figure 4:
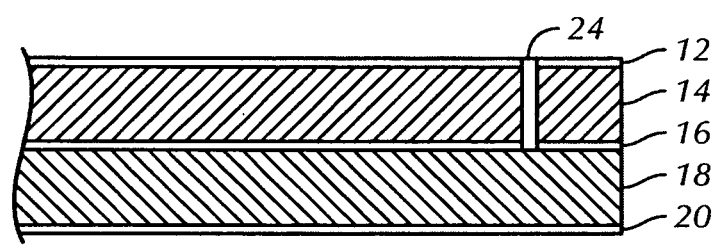
FIG. 4 is a cross sectional view of the preferred embodiment of the RFII antenna assembly taken through section B-B.
Figure 5:
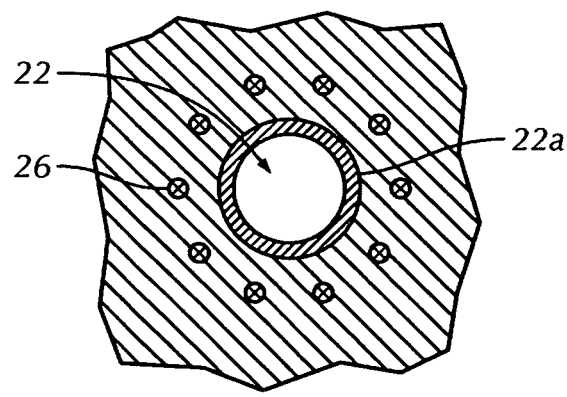
FIG. 5 is a cross sectional view of the preferred embodiment of the RFII antenna assembly taken through section C-C.

Like a conventional one-quarter wave patch antenna, the antenna 32 has two edges 25a, 25b in which the antenna layer 12 is conductively connected to the ground layer 16 and two edges 26a, 26b that are open with a bare dielectric margin area surrounding the copper of the antenna layer 12 and the ground layer 16. In the preferred embodiment, as shown in FIG. 4, the conductive connection between the antenna layer 12 and the ground layer 16 is by a series of plated through holes 24 of preferably a nominal 0.02 inch diameter. The series of plated through holes 24 serve to provide a short circuit connection between the antenna layer 12 and the ground layer 16 at the two shorter sides of the antenna 32 to force the antenna 32 into a quarter-wave mode of operation.

As shown in FIGS. 3 and 6, a through hole 22 is located in the antenna layer 12 along a horizontal centerline and approximately 7 mm from a vertical centerline of the antenna 32. The hole 22 extends through the RFII antenna assembly 10. The diameter of the hole 22 is nominally 0.056 inches for accepting the center conductor of a connector, such as an SMA connector, when the connector is temporarily fastened on the top side of the RFII assembly 10 for testing the antenna 32. The sides 22a of the hole 22 are plated with an electrically conducting material (i.e. forming a plated through hole) for conducting radio signals between the antenna layer 12 and transmitter receiver components preferably attached to the circuit layer 20 at the top side of the RFII antenna assembly 10. FIG. 3 and also shows the plated through holes 26 preferably of nominal 0.02 inch diameter which extend through the PCB layer 18 to connect the ground portion of the printed circuit layer 20 and the antenna ground layer 16. As shown in FIG. 3, the plated through holes 26 surround the plated through hole 22. The combination of the plated through hole 22 and the plated through holes 26 form a microstrip waveguide structure for conducting the radio signals between the antenna layer 12 and transmitter and receiver components attached to the printed circuit layer 20.

In the preferred embodiment of the RFII antenna 32, the hole 22 is located so as to provide a driving point impedance which provides the strongest reflected radio frequency interrogation signal when measuring cardiac impedance. In the preferred embodiment of the antenna 32, the driving point impedance is selected to be approximately 50 ohms when the patient's torso is within the near field of the antenna 32, but could be another impedance value.

In free space, the radiation pattern of the antenna 32 is substantially omni-directional in a plane parallel to the antenna 32 and has a maximum gain of approximately −10 dB. Preferably, the free space return loss of the antenna 32 is approximately −2.7 dB. Preferably, when the antenna 32 is positioned in the range of 1 to 5 mm relative to the thorax, the antenna 32 has a return loss of better than −20 dB. However, a return loss as poor as −10 dB is within the spirit and scope of the invention. Preferably, the tuned antenna 32 has a 10 dB bandwidth of approximately 30 MHz in free space and approximately 14 MHz when positioned within 5 mm of a patient's thorax. Preferably, the amount of RF energy entering the human body is calculated to be 45% of the power coming from the antenna 32. Preferably, the antenna 32 has its best performance when it is positioned within 5 mm of the thorax, but the antenna 32 is still useful at distance up to 200 mm from the thorax.

PCT/US2007/020473 filed Sep. 21, 2007, entitled "Apparatus and Method for Non-invasive Thoracic Radio Interrogation"; U.S. Provisional application No. 60/846,402 entitled "Method for Conditioning Radio Signal Returns from Thoracic Components for Extractions of Cardiopulmonary Data", filed Sep. 21, 2006; U.S. Provisional application No. 60/846,403, entitled "Method and Apparatus for Non-Invasive Bio Impedance Determination", filed Sep. 21, 2006; and U.S. Provisional application No. 60/973,985, entitled "Apparatus and Method for Non-Invasive Thoracic Radio Interrogation", filed Sep. 20, 2007 are all incorporated by reference herein in their entirety.

It will be appreciated by those skilled in the art that changes could be made to the embodiments described above without departing from the broad inventive concept thereof. This invention is not limited to the particular embodiments disclosed.

I claim:

1. A bi-directional, near field, ultra high frequency human thoracic radio interrogation antenna assembly comprising:
   an antenna layer,
   a ground layer and
   a dielectric layer between the antenna layer and the ground layer, each of the antenna layer and the ground layer forming a four sided figure in the shape of two identical mirror image right triangles joined together symmetrically at a hypotenuse of each one of the triangle, the three sides of each triangle being of a different length and the antenna layer and the ground layer being electrically connected together along an adjacent two shortest sides of the figure.

2. The antenna of claim 1 wherein at least one interior angle of each triangle is in the range of 31-44 degrees.

3. The antenna of claim 1 wherein at least one interior angle of each triangle is in the range of 35-40 degrees.

4. The antenna of claim 1, wherein the electrical connection connecting the antenna layer and the ground layer is by a plurality of plated through holes along the adjacent two shortest sides of each kite-shaped figure.

5. The antenna of claim 4 wherein a conductive connection with the antenna layer for exciting the antenna layer is formed by a microstrip waveguide through the dielectric layer.

6. The antenna of claim 5, wherein the conductive connection for exciting the antenna layer is a plated through hole.

7. The antenna of claim 6, wherein the conductive connection for exciting the antenna layer is positioned at a location along a central axis of symmetry of the kite-shaped figure selected to maximize a return loss of the antenna when the antenna is positioned sufficiently proximate to a human subject thorax for near field operation into and from the thorax.

8. The antenna of claim 1, wherein the antenna is resonant within the range of 902-928 MHz.

9. The antenna of claim 8, wherein each kite-shaped figure has a length along an axis of symmetry of about two inches and at least one interior angle within a range of between 70 and 80 degrees.

10. The antenna of claim 1, each triangle is approximately a three-four-five right triangle.

11. The antenna of claim 1, wherein each figure has a surface area of less than two square inches.

12. The antenna of claim 1 operably connected in an assembly with a hemodynamic measurement system configured to generate a radio frequency interrogation signal and to receive and process reflections of the radio frequency interrogation signal from a human subject.

13. The assembly of claim 12 wherein the antenna is operably connected with a radio transmitter and a radio receiver of the measurement system.

14. The antenna assembly of claim 13, wherein the antenna is a quarter-wave antenna designed for an operating frequency within the 902-928 MHz ISM band.

15. The assembly of claim 12 wherein the measurement system adjoins one side of the ground layer and is separated from the ground layer by at least a dielectric layer.

16. The antenna assembly of claim 1 in combination with an ultra-high frequency radio transmitter operating in the 902-928 MHz band and a radio receiver both supported from the antenna assembly on a ground layer side of the antenna assembly, the radio transmitter and receiver both being operably connected with the antenna layer through the ground layer and dielectric layer.

17. The antenna assembly of claim 16 wherein the radio transmitter is configured to transmit an unmodulated ultra-high frequency signal of no more than one milliwatt from the antenna layer.

18. The antenna of claim 17 wherein each triangle is a right triangle.

19. The antenna of claim 17 wherein the antenna layer and the ground layer are electrically connected together at each of an adjacent two of the sides of the figure.

20. The antenna of claim 1 wherein the ground layer is identical in shape, orientation and surface area dimension to the antenna layer.

21. In a system with a radio transmitter and radio receiver for radio hemodynamic monitoring of a human subject by near field transmission of a radio interrogation signal into a thorax of a subject and capture of reflections of the radio interrogation signal from tissues of the thorax through one antenna, the one antenna comprising:
    an antenna layer;
    a ground layer; and
    a dielectric layer between the antenna layer and the ground layer, each of the antenna layer and the ground layer forming a kite-shaped figure of two identical mirror image triangles joined together symmetrically at a longest side of each one of the triangles, the three sides of each triangle being of a different length.

22. The antenna of claim 21 operably connected with the radio transmitter and receiver, the radio transmitter being configured to transmit an unmodulated ultra-high frequency signal at a power of no more than about one milliwatt from the antenna layer.

* * * * *